(12) United States Patent
Meng et al.

(10) Patent No.: US 12,115,340 B2
(45) Date of Patent: Oct. 15, 2024

(54) PERISTALTIC PUMPING SEGMENT WITH CHECK VALVE

(71) Applicant: CareFusion 303, Inc., San Diego, CA (US)

(72) Inventors: Fanqing Meng, Buffalo Grove, IL (US); Marc Weimer, South Jordan, UT (US)

(73) Assignee: CareFusion 303, Inc., San Diego, CA (US)

( * ) Notice: Subject to any disclaimer, the term of this patent is extended or adjusted under 35 U.S.C. 154(b) by 539 days.

(21) Appl. No.: 17/183,177

(22) Filed: Feb. 23, 2021

(65) Prior Publication Data

US 2021/0268173 A1     Sep. 2, 2021

Related U.S. Application Data

(60) Provisional application No. 62/982,585, filed on Feb. 27, 2020.

(51) Int. Cl.
*A61M 5/142* (2006.01)
*A61M 5/168* (2006.01)

(52) U.S. Cl.
CPC .... *A61M 5/14212* (2013.01); *A61M 5/16809* (2013.01); *A61M 5/16881* (2013.01)

(58) Field of Classification Search
CPC .......... A61M 5/14212; A61M 5/16809; A61M 5/16881; F04B 43/123; F04B 43/082;
(Continued)

(56) References Cited

U.S. PATENT DOCUMENTS 4,391,600 A * 7/1983 Archibald ............. A61M 5/168
                                                            417/63
4,946,448 A   8/1990 Richmond
(Continued)

FOREIGN PATENT DOCUMENTS

EP           2011438 A2    1/2009
WO    WO-2010019470 A1    2/2010
(Continued)

OTHER PUBLICATIONS

International Search Report and Written Opinion for Application No. PCT/US2021/019104, dated Apr. 13, 2021, 16 pages.

*Primary Examiner* — Scott J Medway
*Assistant Examiner* — Anh Bui
(74) *Attorney, Agent, or Firm* — Morgan, Lewis & Bockius LLP (57) ABSTRACT

Pumping segments are described herein. In certain embodiments, a peristaltic pumping segment include a tubing segment, a plunger, a downstream occluder, and an upstream check valve. The plunger is movable to selectively expand the pumping volume to draw in fluid flow and contract the pumping volume to administer the fluid flow. The occluder is movable to selectively engage against the downstream portion to prevent fluid flow from the downstream portion during expansion of the pumping volume and to permit fluid flow from the pumping volume through the downstream portion during contraction of the pumping volume. The check valve outlet is in fluid communication with the pumping volume, and the valve element is configured to permit fluid flow from the valve inlet to the pumping volume during expansion of the pumping volume and to prevent fluid flow from the pumping volume to the valve inlet during contraction of the pumping volume.

7 Claims, 3 Drawing Sheets

(58) Field of Classification Search
CPC .. F04B 43/12; F04B 43/1238; F04B 43/1246; F04B 43/1253; F04B 43/1261; F04B 45/06

See application file for complete search history.

(56) References Cited

U.S. PATENT DOCUMENTS

| | | | |
|---|---|---|---|
| 5,697,915 | A | 12/1997 | Lynn |
| 10,202,971 | B2 | 2/2019 | Kamen et al. |
| 2010/0106082 | A1 | 4/2010 | Zhou |
| 2011/0198241 | A1* | 8/2011 | Murakami ......... G01N 27/3274 205/792 |

FOREIGN PATENT DOCUMENTS

| | | |
|---|---|---|
| WO | WO-2011094798 A1 | 8/2011 |
| WO | WO-2011124388 A1 | 10/2011 |

* cited by examiner

PERISTALTIC PUMPING SEGMENT WITH CHECK VALVE

REFERENCE TO RELATED APPLICATIONS

This application claims priority to U.S. Provisional Patent Application No. 62/982,585, filed Feb. 27, 2020, the entire disclosure of each of these applications being incorporated herein by this reference.

FIELD OF THE INVENTION

The present disclosure generally relates to pumping segments, and, in particular, to peristaltic pumping segments.

BACKGROUND

Patients in hospitals often receive medications and medical fluids (e.g., a saline solution or a liquid medication) via infusion using an intravenous ("IV") pump. In some applications, an IV pump uses peristaltic manipulation of a segment of tubing of an IV set to create the flow of medical fluid to the patient. Peristaltic manipulation of a segment of tubing may utilize the material properties of the tubing during operation.

SUMMARY

In some applications, the material properties of the tubing may limit the fluid delivery accuracy of a peristaltic pump.

The disclosed subject matter relates to pumping segments. In certain embodiments, a peristaltic pumping segment include a tubing segment, a plunger, an occluder, and a check valve. The tubing segment defines a pumping volume between an upstream portion and a downstream portion. The plunger is disposed adjacent to the pumping volume of the tubing segment. The plunger is movable to selectively expand the pumping volume to draw in fluid flow and contract the pumping volume to administer the fluid flow. The occluder is disposed adjacent to the downstream portion of the tubing segment. The occluder is movable to selectively engage against the downstream portion to prevent fluid flow from the downstream portion during expansion of the pumping volume and to permit fluid flow from the pumping volume through the downstream portion during contraction of the pumping volume. The check valve is coupled to the upstream portion of the tubing segment, the check valve comprising a valve element in fluid communication with a valve inlet and a valve outlet. The valve outlet is in fluid communication with the pumping volume, and the valve element is configured to permit fluid flow from the valve inlet to the pumping volume during expansion of the pumping volume and to prevent fluid flow from the pumping volume to the valve inlet during contraction of the pumping volume.

In certain embodiments, a fluid delivery system includes a fluid container including a medical fluid, an intravenous tubing, and an intravenous pump. The intravenous pump includes a tubing segment, a plunger, an occluder, and a check valve. The tubing segment defines a pumping volume between an upstream portion and a downstream portion, wherein the downstream portion is in fluid communication with the intravenous tubing. The plunger is disposed adjacent to the pumping volume of the tubing segment. The plunger is movable to selectively expand, or permit expansion of, the pumping volume to draw in the medical fluid from the fluid container and contract the pumping volume to administer the medical fluid to the intravenous tubing. The occluder is disposed adjacent to the downstream portion of the tubing segment. The occluder is movable to selectively engage against the downstream portion to prevent fluid flow from the intravenous tubing during expansion of the pumping volume and to permit fluid flow from the pumping volume through the intravenous tubing during contraction of the pumping volume. The check valve is coupled to the upstream portion of the tubing segment, the check valve comprising a valve element in fluid communication with a valve inlet and a valve outlet. The valve inlet is in fluid communication with the fluid container, the valve outlet is in fluid communication with the pumping volume, and the valve element is configured to permit fluid flow from the fluid container to the pumping volume during expansion of the pumping volume and to prevent fluid flow from the pumping volume toward the fluid container during contraction of the pumping volume.

In certain embodiments, a method is disclosed and comprises expanding a pumping volume of a tubing segment; and drawing a medical fluid through a check valve into the pumping volume during the expanding the pumping volume.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to administration of medical fluid by utilizing the disclosed peristaltic pumping segment, it is to be understood that this description is only an example of usage and does not limit the scope of the claims. Various aspects of the disclosed peristaltic pumping segments may be used in any application where it is desirable to administer the flow of fluid.

Figure 1:
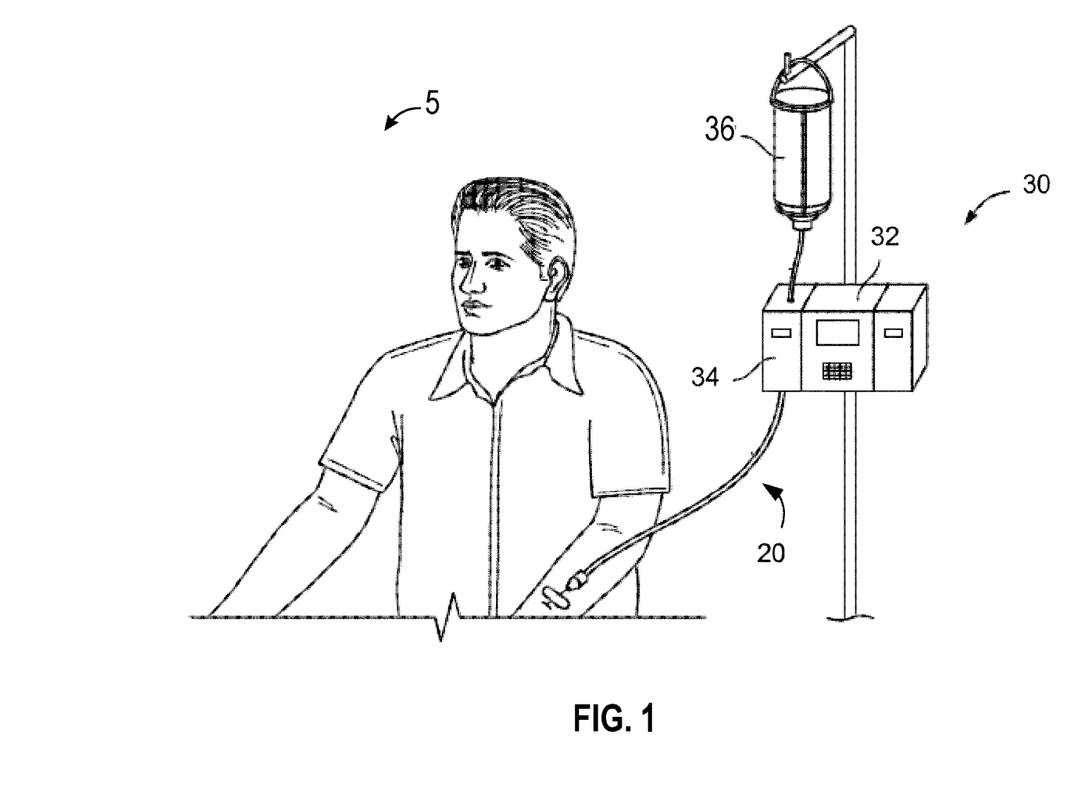
FIG. 1 depicts a patient receiving an infusion of a medical fluid using an IV pump.

FIG. 1 depicts a patient 5 receiving an infusion of a medical fluid using an IV pump 30. In the depicted example, the IV pump 30 is delivering a medical fluid from a fluid container 36 to the patient 5. A fluid container 36 is hung at or above the patient's head and connected via an IV set 20 to the IV pump module 34 and then to the patient 5. In some embodiments, the IV pump 30 includes a control unit 32 and a pumping module 34.

The pumping module 34 can include a peristaltic pump segment to administer the medical fluid from the fluid container 36 to the patient 5.

Figure 2A:
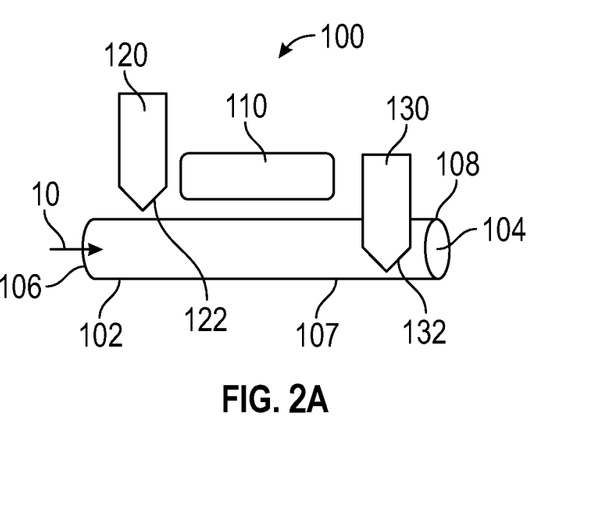
FIG. 2A is an illustration of a peristaltic pump segment in a filling phase, in accordance with various aspects of the present disclosure.

FIG. 2A is an illustration of a peristaltic pump segment 100 in a filling phase, in accordance with various aspects of the present disclosure. As illustrated, a peristaltic pump segment 100 can include tubing 102 that is peristaltically manipulated to create the flow of medical fluid to the patient. In some embodiments, an upstream portion 106 of the tubing 102 is in fluid communication with a source of medical fluid, such as an IV bag or other medical fluid container, and the downstream portion 108 of the tubing is in fluid communication with IV tubing to the patient.

In some embodiments, peristaltic pumping repeatedly cycles between a filling phase and a delivery phase.

In some applications, a peristaltic pump segment 100 can include a plunger 110, an upstream occluder 120, and a downstream occluder 130, each configured to contact and manipulate the tubing 102 to deliver fluid from a fluid source to the patient. In some embodiments, the plunger 110, the upstream occluder 120, and the downstream occluder 130 can move in coordinated, sequential steps to pump fluid through the tubing 102. The tubing 102 can be formed from a mechanically resilient material such as polyvinyl chloride (PVC), thermoplastic elastomer (TPE), thermoplastic polyurethane (TPU), polyolefin, silicone, composites thereof, or the like.

With reference to FIG. 2A, the tubing 102 draws in medical fluid 10 during the filling phase. As illustrated, the plunger 110 is withdrawn or retracted from a compressed portion of the tubing 102, allowing the tubing walls 104 to resiliently expand the pumping volume 107 to an original or expanded state. The plunger 110 can be moved by a suitable mechanism, including one or more of an actuator, a cam assembly, a geared assembly, or the like.

In the depicted example, the expansion of the pumping volume 107 draws in fluid into the peristaltic pump segment 100, and in particular, the pumping volume 107. The mechanical resilience of the tubing 102 allows the tubing walls 104 to expand from a compressed state to an expanded state, expanding the pumping volume 107. The rate at which the pumping volume 107 rebounds from a compressed state to an expanded state can determine the amount of fluid that can be drawn into the pumping volume 107 in a given period of time.

As illustrated, during the expansion of the pumping volume 107, the downstream portion 108 of the tubing 102 is blocked, pinched, or otherwise occluded by the downstream occluder 130 to prevent backflow or contamination of fluid into the pumping volume 107.

In the depicted example, the downstream occluder 130 is actuated, moved downward, or otherwise engaged to compress the tubing walls 104 of the tubing 102 at the downstream portion 108 to occlude flow through the downstream portion 108 of the tubing 102. The downstream occluder 130 can be moved by any suitable mechanism, including an actuator, a cam assembly, a geared assembly, etc. The downstream occluder 130 can include a beveled engagement portion 132 to contact the tubing 102. When engaged, the downstream occluder 130 can prevent flow or fluid communication from the downstream portion 108 into the pumping volume 107.

During the expansion of the pumping volume 107, medical fluid 10 is drawn into pumping volume 107 from the upstream portion 106 of the tubing 102. As illustrated, during the expansion of the pumping volume 107, the upstream portion 106 of the tubing 102 is unobstructed by the upstream occluder 120, permitting medical fluid 10 into the pumping volume 107. During operation, the upstream occluder 120 is withdrawn or retracted from a compressed portion of the tubing 102, allowing the tubing walls 104 to resiliently expand the upstream portion 106 to an original or expanded state. The upstream occluder 120 can be moved by a suitable mechanism, including one or more of an actuator, a cam assembly, a geared assembly, or the like.

In the depicted example, the expansion of the upstream portion 106 permits the flow of medical fluid 10 into the peristaltic pump segment 100, and in particular, the pumping volume 107. The mechanical resilience of the tubing 102 allows the tubing walls 104 to expand from a compressed state to an expanded state, expanding the cross-sectional profile or flow area of the upstream portion 106. The rate at which the upstream portion 106 rebounds from a compressed state to an expanded state can limit the size of the flow area or opening into the pumping volume 107. Therefore, the rate at which the upstream portion 106 rebounds from a compressed state to an expanded state can limit or restrict the amount of fluid that can be drawn into the pumping volume 107 in a given period of time.

The amount of medical fluid 10 drawn into the pumping volume 107 during the filling phase can be determined by the timing and sequence of the plunger 110, the upstream occluder 120, a viscosity of the medical fluid 110, and the mechanical properties of the tubing 102.

Figure 2B:
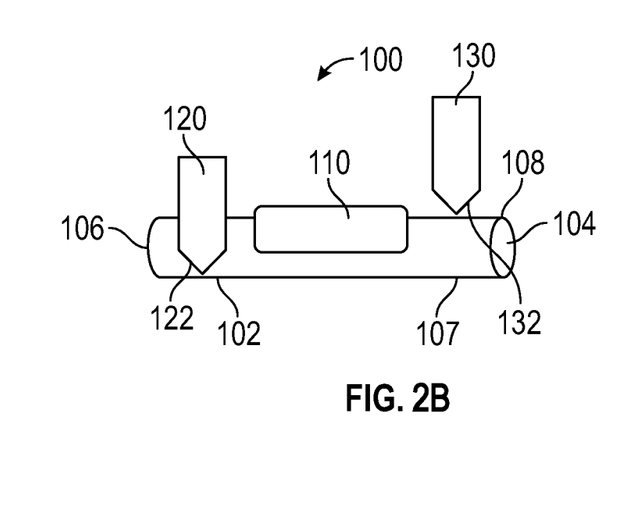
FIG. 2B is an illustration of a peristaltic pump segment of FIG. 2A in a delivery phase, in accordance with various aspects of the present disclosure.

FIG. 2B is an illustration of a peristaltic pump segment 100 of FIG. 2A in a delivery phase, in accordance with various aspects of the present disclosure.

In the depicted example, the peristaltic pumping segment 100 delivers medical fluid through a downstream portion 108 to a downstream location, such as a patient. As illustrated, the plunger 110 is actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. The rate of administration of the medical fluid can be controlled by the force and velocity of the plunger 110.

During administration, the upstream portion 106 of the tubing 102 is blocked, pinched, or otherwise occluded by the upstream occluder 120 to prevent inadvertent fluid flow into the pumping volume 107 and to prevent backflow of fluid into the medical container from the pumping volume 107.

In the depicted example, the upstream occluder 120 is actuated, moved downward, or otherwise engaged to compress the tubing walls 104 of the tubing 102 at the upstream portion 106 to occlude flow through the upstream portion 106 of the tubing 102. The upstream occluder 120 can include a beveled engagement portion 122 to contact the tubing 102. When engaged, the upstream occluder 120 can prevent flow or fluid communication between the upstream portion 106 and the pumping volume 107.

During the compression of the pumping volume 107, medical fluid is forced from the pumping volume 107 to a downstream location through the downstream portion 108 of the tubing 102. As illustrated, during the compression of the pumping volume 107, the downstream portion 108 of the tubing 102 is unobstructed by the downstream occluder 130, permitting medical fluid 10 to flow out of the peristaltic pumping segment 100. During operation, the downstream occluder 130 is withdrawn or retracted from a compressed portion of the tubing 102, allowing the tubing walls 104 to resiliently expand the downstream portion 108 to an original or expanded state.

In the depicted example, the expansion of the downstream portion 108 permits the flow of medical fluid 10 out of the peristaltic pump segment 100, and in particular, the pumping volume 107. The mechanical resilience of the tubing 102 allows the tubing walls 104 to expand from a compressed state to an expanded state, expanding the cross-sectional profile or flow area of the downstream portion 108. The rate at which the downstream portion 108 rebounds from a compressed state to an expanded state can limit the size of the flow area or opening out of the pumping volume 107. Therefore, the rate at which the downstream portion 108 rebounds from a compressed state to an expanded state can limit or restrict the amount of fluid that can flow out of the pumping volume 107 in a given period of time.

The amount of medical fluid 10 administered from the pumping volume 107 during the delivery phase can be determined by the timing and sequence of the plunger 110, the downstream occluder 130 and the mechanical properties of the tubing 102.

In some applications, it may be desirable to perform peristaltic pumping operations at high flow rates (up to 1200 mL/hr) across a wide range of temperatures (5 C to 40 C). As described herein, the upstream portion of the tubing may be required to rebound from a compressed state to an expanded state rapidly (in a sub-second time scale) to facilitate high flow rates. However, materials used for tubing (e.g., polyvinyl chloride (PVC), thermoplastic elastomer (TPE), thermoplastic polyurethane (TPU), polyolefin, silicone, etc.) can become rigid at lower temperatures and deteriorate in elasticity. Therefore, the upstream portion of the tubing may rebound from a compressed state to an expanded state at a slower rate than required to facilitate high flow rates. In some applications, the amount of fluid drawn into the pumping volume of the tubing during expansion may be reduced at low temperatures, resulting in under volume delivery.

In some applications, it may be desirable to perform peristaltic pumping operations at low flow rates (as low as 0.1 mL/hr) across a wide range of temperatures (5 C to 40 C). As described herein, the upstream portion of the tubing may be required to rebound from a compressed state to an expanded state slowly to facilitate low flow rates. However, PVC tubing may exhibit surface tackiness due to exuded small molecular plasticizers on the inner and outer layer surface of the tubing, which may cause the tubing walls to adhere together at higher temperatures. Therefore, the upstream portion of the tubing may rebound from a compressed state to an expanded state at a slower rate than required or may remain in a compressed or occluded state. In some applications, the amount of fluid drawn into the pumping volume of the tubing during expansion may be reduced at low flow rates at high temperatures, resulting in under volume delivery.

The disclosed peristaltic pump segment incorporates a check valve to allow for improved fluid delivery accuracy. By utilizing a check valve in the peristaltic pump segment, the peristaltic pump segment can provide consistent and accurate fluid delivery by reducing or eliminating undesired flow caused by unpredictable rebounding of the segment, which may vary based on temperature and pumping frequency.

The disclosed peristaltic pumping segment overcomes several challenges discovered with respect to certain conventional peristaltic pumping segments and systems. One challenge with certain conventional peristaltic pumping segment is that certain conventional peristaltic pumping segment rely on the material properties of the tubing to draw fluid volume into the pumping segment. Further, certain peristaltic pumping segments or systems may require numerous moving parts during operation such as occluders to control the flow of fluid from a source to a patient. Because material properties of tubing may vary with temperature and pumping frequency, decreasing accuracy, and numerous moving parts can increase complexity, power consumption, and wear, it is advantageous to provide peristaltic pumping segments and systems, as described herein, that allow for increased fluid delivery accuracy, less wear on the tubing, fewer mechanical parts, and lower power consumption. The disclosed peristaltic pumping segments provide for increased fluid delivery accuracy, less wear on the tubing, fewer mechanical parts, and lower power consumption.

Examples of peristaltic pumping segments that allow for increased fluid delivery accuracy and reduced complexity are now described.

Figure 3A:
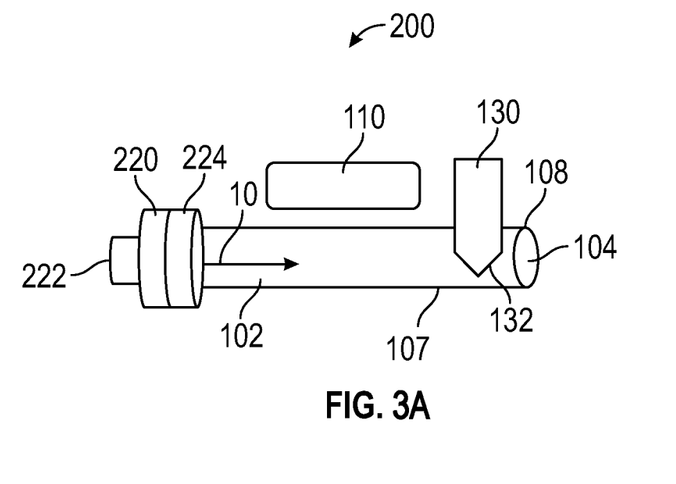
FIG. 3A is an illustration of a peristaltic pump segment in a filling phase, in accordance with various aspects of the present disclosure.

FIG. 3A is an illustration of a peristaltic pump segment 200 in a filling phase, in accordance with various aspects of the present disclosure. As illustrated, a peristaltic pump segment 200 can include tubing 102 that is peristaltically manipulated to create the flow of medical fluid to the patient. As described herein, the flow of medical fluid is controlled by a check valve 220 coupled to the tubing 102. In some embodiments, a valve inlet 222 of the check valve 220 is in fluid communication with a source of medical fluid, such as a medical fluid container. The valve outlet 224 of the check valve 220 is in fluid communication with a pumping volume 107 of the tubing 102. In some embodiments, the downstream portion 108 of the tubing 102 is in fluid communication with IV tubing to the patient.

In some embodiments, peristaltic pumping cycles between a filling phase and a delivery phase.

In some applications, a peristaltic pump segment 200 can include a plunger 110 and a downstream occluder 130 configured to contact and manipulate the tubing 102 to deliver fluid from a fluid source to the patient. In some embodiments, the plunger 110 and the downstream occluder 130 can move in coordinated, sequential steps to pump fluid through the tubing 102. The check valve 220 can control flow through the tubing 102 during the pumping process to allow flow from a medical fluid source into the tubing 102, while preventing backflow from the tubing 102 into the medical fluid source. The tubing 102 can be formed from a mechanically resilient material such as polyvinyl chloride (PVC), thermoplastic elastomer (TPE), thermoplastic polyurethane (TPU), polyolefin, silicone, composites thereof, or the like.

The features shown in FIG. 3A also reduce the need for an upstream occluder, such as the occluder 120 shown in FIGS. 2A, and 2B. If the pumping segment includes an in-line valve as described and shown, for example, in FIG. 3A, the pump may omit the upstream occluder along with the complexities and resource management required to adjust the functioning thereof. For example, additional power and processing cycles may be needed to control the upstream occluder. Use of these resources along with friction associated with, for example, pressing against the tubing may increase the temperature thereby introducing the potential for additional rebound effects.

In some implementations, the pump may selectively enable an upstream occluder based on the set loaded into the pump. For example, the set may include an identifier that can be detected upon insertion to the pump. In some implementations, the pump may request a user input during programming to identify the set being loaded. If the set is identified as a type with the in-line check valve features described, the pump may disable the upstream occluder to reduce resources needed for the infusion and strain on the pumping segment. By disabling the upstream occluder, the sources of temperature variance may be reduced. However, if the set is identified as a type without the in-line features described, the pump may enable the upstream occluder.

With reference to FIG. 3A, the tubing 102 draws in medical fluid 10 during the filling phase. As illustrated, the plunger 110 is withdrawn or retracted from a compressed portion of the tubing 102, allowing the tubing walls 104 to resiliently expand the pumping volume 107 to an original or expanded state. As can be appreciated, the plunger 110 can be moved by a suitable mechanism, including one or more of an actuator, a cam assembly, a geared assembly, or the like.

In the depicted example, the expansion of the pumping volume 107 draws in fluid into the peristaltic pump segment 100, and in particular, the pumping volume 107. As can be appreciated, the mechanical resilience of the tubing 102 allows the tubing walls 104 to expand from a compressed state to an expanded state, expanding the pumping volume 107. The rate at which the pumping volume 107 rebounds from a compressed state to an expanded state can determine the amount of fluid that can be drawn into the pumping volume 107 in a given period of time.

As illustrated, during the expansion of the pumping volume 107, the downstream portion 108 of the tubing 102 is blocked, pinched, or otherwise occluded by the downstream occluder 130 to prevent backflow or contamination of fluid into the pumping volume 107.

In the depicted example, the downstream occluder 130 is actuated, moved downward, or otherwise engaged to compress the tubing walls 104 at the downstream portion 108 to occlude flow through the downstream portion 108 of the tubing 102. The downstream occluder 130 can be moved by a suitable mechanism, including one or more of an actuator, a cam assembly, a geared assembly, or the like. The downstream occluder 130 can include a beveled engagement portion 132 to contact the tubing 102. When engaged, the downstream occluder 130 can prevent flow or fluid communication from the downstream portion 108 into the pumping volume 107.

During the expansion of the pumping volume 107, medical fluid 10 is drawn into pumping volume 107 through the check valve 220 coupled to the tubing 102. As illustrated, during the expansion of the pumping volume 107, the check valve 220 allows for medical fluid 10 to flow from the valve inlet 222 to the valve outlet 224, permitting medical fluid 10 into the pumping volume 107. During operation, a valve element within the check valve 220 is actuated or moved to permit flow from the valve inlet 222 toward the valve outlet 224. In some implementations, the valve element can be spring actuated, or passively actuated with using a flap, ball and socket, or other means to fluid to flow only one direction.

In the depicted example, the actuation of the valve element within the check valve 220 to permit flow between the valve inlet 222 and the valve outlet 224 permits the flow of medical fluid 10 into the peristaltic pump segment 100, and in particular, the pumping volume 107. As can be appreciated, the valve element can be actuated by a pressure differential across the valve inlet 222 and the valve outlet 224. For example, as the pumping volume 107 expands, the increasing volume of the pumping volume 107 can create a pressure differential across the valve inlet 222 and the valve outlet 224, actuating the valve element and permitting flow into the pumping volume 107. Optionally, positive pressure (e.g., by changing the height of the fluid container relative to the pump) can be applied at a fluid source to create a pressure differential across the valve inlet 222 and the valve outlet 224.

In some embodiments, the check valve 220 can have a threshold pressure or cracking pressure that actuates the valve element to permit flow from the valve inlet 222 to the valve outlet 224. Optionally, the cracking pressure can be selected based on flow requirements, temperature, tubing selection, etc. In some embodiments, the check valve 220 can have a valve element controlled by an actuator and/or a controller. The rate of actuation of the valve element from an occluding state to a flow state can control the amount of fluid that can be drawn into the pumping volume 107 in a given period of time. Advantageously, the valve element of the check valve 220 can be rapidly actuated independent of the mechanical properties (e.g. resilience) of the tubing 102, allowing the check valve 220 to permit a desired amount of fluid into the pumping volume 107 independent of temperature, tubing material, and/or flow rates.

The amount of medical fluid 10 drawn into the pumping volume 107 during the filling phase can be determined by the timing and sequence of the plunger 110, the characteristics of the check valve 220 and the mechanical properties of the tubing 102.

Figure 3B:
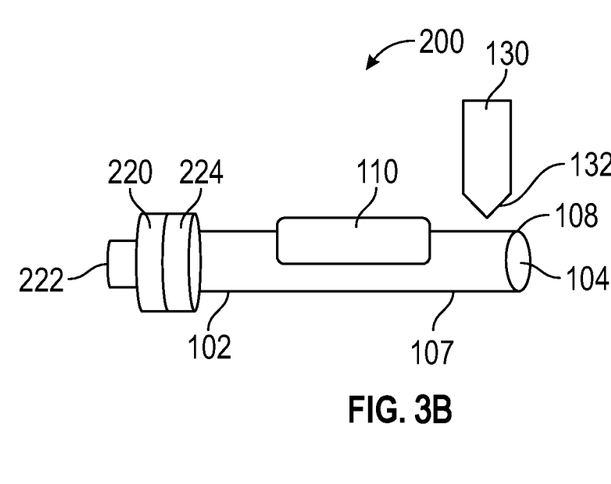
FIG. 3B is an illustration of a peristaltic pump segment of FIG. 3A in a delivery phase, in accordance with various aspects of the present disclosure.

FIG. 3B is an illustration of a peristaltic pump segment 200 of FIG. 3A in a delivery phase, in accordance with various aspects of the present disclosure.

In the depicted example, the peristaltic pumping segment 200 delivers medical fluid through a downstream portion 108 to a downstream location, such as a patient. As illustrated, the plunger 110 is actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. The rate of administration of the medical fluid can be controlled by the force and velocity of the plunger 110.

During administration, the flow through the check valve 220 is blocked or occluded to prevent inadvertent fluid flow into the pumping volume 107 and to prevent backflow of fluid from the pumping volume 107 back into the medical container. During administration, the check valve 220 prevents or restricts the backflow of medical fluid from the valve outlet 224 toward the valve inlet 222. The check valve 220 further prevents or restricts inadvertent flow of medical fluid from the valve inlet 222 to the valve outlet 224.

The valve element can be configured to remain in an occlusion position when a pressure differential is applied across the valve outlet 224 and the valve inlet 222. For example, when the pumping volume 107 is moved to a compressed configuration, the valve element can prevent the backflow of fluid from the valve outlet 224 toward the valve inlet 222.

The valve element can be configured to remain in an occlusion position in the absence of a pressure differential. For example, when the pumping volume 107 is at a resting or expanded configuration, the valve element can prevent the backflow of fluid from the valve outlet 224 toward the valve inlet 222. Further, the valve element can be configured to remain in an occlusion position if a pressure differential across the valve inlet 222 and the valve outlet 224 does not exceed the cracking pressure of the check valve 220. For example, the valve element can prevent the inadvertent flow of medical fluid into the pumping volume 107 when the pumping volume 107 is in a resting (e.g., expanded) position.

During the compression of the pumping volume 107, medical fluid is forced from the pumping volume 107 to a downstream location through the downstream portion 108 of the tubing 102. As illustrated, during the compression of the pumping volume 107, the downstream portion 108 of the tubing 102 is unobstructed by the downstream occluder 130, permitting medical fluid 10 to flow out of the peristaltic pumping segment 200. During operation, the downstream occluder 130 is withdrawn or retracted from a compressed portion of the tubing 102, allowing the tubing walls 104 to resiliently expand the downstream portion 108 to an original or expanded state.

In the depicted example, the expansion of the downstream portion 108 permits the flow of medical fluid 10 out of the peristaltic pump segment 200, and in particular, the pumping volume 107. The mechanical resilience of the tubing 102 allows the tubing walls 104 to expand from a compressed state to an expanded state, expanding the cross-sectional profile or flow area of the downstream portion 108. The rate at which the downstream portion 108 rebounds from a compressed state to an expanded state can limit the size of the flow area or opening out of the pumping volume 107. Therefore, the rate at which the downstream portion 108 rebounds from a compressed state to an expanded state can limit or restrict the amount of fluid that can flow out of the pumping volume 107 in a given period of time.

The amount of medical fluid 10 administered from the pumping volume 107 during the delivery phase can be determined by the timing and sequence of the plunger 110, the downstream occluder 130 and the mechanical properties of the tubing 102.

In some embodiments, the downstream occluder 130 can be replaced with a check valve. A downstream check valve can be configured to have a cracking pressure to permit desired outflow from the pumping volume 107 while preventing backflow from downstream locations.

In some applications, the peristaltic pump segment 200 can be utilized in pump modules configured for use with upstream occluders and downstream occluders by disabling operation of the upstream occluder.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

Various examples of aspects of the disclosure are described below as clauses for convenience. These are provided as examples, and do not limit the subject technology.

Clause 1. A peristaltic pumping segment comprising: a tubing segment defining a resilient pumping volume between an upstream portion and a downstream portion of the tubing segment, the pumping volume being selectively engagable by a plunger disposed adjacent to the pumping volume of the tubing segment, wherein the pumping volume is selectively engaged by the plunger to expand the pumping volume to draw fluid flow into the pumping volume and to contract the pumping volume to conduct fluid flow from the pumping volume; and a check valve coupled to the upstream portion of the tubing segment, the check valve comprising a valve element in fluid communication with a valve inlet and a valve outlet, wherein the valve outlet is in fluid communication with the pumping volume, and the valve element is configured to permit fluid flow from the valve inlet to the pumping volume during expansion of the pumping volume and to prevent fluid flow from the pumping volume to the valve inlet during contraction of the pumping volume.

Clause 2. The peristaltic pumping segment of Clause 1, wherein the downstream portion of the tubing segment is selectively engagable by an occluder disposed adjacent to the downstream portion, wherein the downstream portion is selectively engaged by the occluder to restrict retrograde fluid flow from the downstream portion into the pumping volume during expansion of the pumping volume and to permit fluid flow from the pumping volume through the downstream portion during contraction of the pumping volume.

Clause 3. The peristaltic pumping segment of Clause 1, wherein the pumping volume is configured to expand upon spacing the plunger apart from the pumping volume.

Clause 4. The peristaltic pumping segment of Clause 1, wherein the tubing segment comprises one or more of polyvinyl chloride, thermoplastic elastomer, thermoplastic polyurethane, polyolefin, and silicone.

Clause 5. The peristaltic pumping segment of Clause 1, wherein the check valve is configured to close after complete expansion of the pumping volume.

Clause 6. The peristaltic pumping segment of Clause 1, wherein the check valve is configured to open after complete contraction of the pumping volume.

Clause 7. The peristaltic pumping segment of Clause 1, wherein the check valve changes between an open configuration and a closed configuration in response to changing pressure differentials across the check valve.

Clause 8. The peristaltic pumping segment of Clause 1, wherein the pumping segment is configured to operate with a peristaltic pump comprising a disabled upstream occluder.

Clause 9. A fluid delivery system comprising: an intravenous tubing configured to be connected to a fluid container comprising a medical fluid; a tubing segment defining a resilient pumping volume between an upstream portion and a downstream portion, wherein the upstream portion is in fluid communication with the intravenous tubing and the downstream portion is compressible to selectively control fluid flow from the pumping volume during expansion and compression of the pumping volume; and a check valve coupled to the upstream portion of the tubing segment, the check valve being configured to selectively control fluid flow between the upstream portion of the tubing segment and the pumping volume, the check valve changing between an open configuration and a closed configuration based on a pressure differential across the check valve, wherein the pumping volume is configured to be compressed by a plunger of a peristaltic pump.

Clause 10. The fluid delivery system of Clause 9, wherein the check valve is configured to close after complete expansion of the pumping volume.

Clause 11. The fluid delivery system of Clause 9, wherein the check valve is configured to open after complete compression of the pumping volume.

Clause 12. The fluid delivery system of Clause 9, wherein the pumping volume is configured to operate with a peristaltic pump comprising a disabled upstream occlude.

Clause 13. A method comprising: expanding a peristaltic pumping volume of a tubing segment; and drawing a medical fluid through a check valve into the pumping volume during the expanding the pumping volume.

Clause 14. The method of Clause 13, further comprising: compressing a downstream portion of the tubing segment to restrict fluid flow from the pumping volume through the downstream portion during the expanding the pumping volume.

Clause 15. The method of Clause 14, further comprising: contracting the pumping volume of the tubing segment to administer the medical fluid through a downstream portion of the tubing segment; and expanding the downstream portion of the tubing segment to permit fluid flow from the pumping volume.

Clause 16. The method of Clause 15, further comprising: changing the check valve between an open configuration and a closed configuration in response to changing pressure differentials across the check valve.

Clause 17. The method of Clause 15, further comprising: moving a plunger to expand and contract the pumping volume of the tubing segment.

Clause 18. The method of Clause 15, further comprising: drawing the medical fluid from a fluid container through the check valve during the expanding the pumping volume.

Clause 19. The method of Clause 15, further comprising: restricting fluid flow from the pumping volume to the fluid container through the check valve during the contracting the pumping volume.

Clause 20. The method of Clause 15, further comprising: resiliently expanding the pumping volume of the tubing segment after the contracting the tubing segment.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

What is claimed is:

1. A peristaltic pumping segment comprising:
   a tubing segment defining a resilient pumping volume between an upstream portion and a downstream portion of the tubing segment, the pumping volume being selectively engagable by a plunger disposed adjacent to the pumping volume of the tubing segment, wherein the pumping volume is selectively engaged by the plunger to expand the pumping volume to draw fluid flow into the pumping volume and to contract the pumping volume to conduct fluid flow from the pumping volume, wherein the downstream portion of the tubing segment is selectively engagable by an occluder disposed adjacent to the downstream portion, wherein the downstream portion is selectively engaged by the occluder to compress the downstream segment to restrict retrograde fluid flow from the downstream portion into the pumping volume during expansion of the pumping volume and to permit fluid flow from the pumping volume through the downstream portion during contraction of the pumping volume; and
   a check valve coupled to the upstream portion of the tubing segment, the check valve comprising a valve element in fluid communication with a valve inlet and a valve outlet, wherein the valve outlet is in fluid communication with the pumping volume, and the valve element is configured to permit fluid flow from the valve inlet to the pumping volume during expansion of the pumping volume and to prevent fluid flow from the pumping volume to the valve inlet during contraction of the pumping volume.

2. The peristaltic pumping segment of claim 1, wherein the pumping volume is configured to expand upon spacing the plunger apart from the pumping volume.

3. The peristaltic pumping segment of claim 1, wherein the tubing segment comprises one or more of polyvinyl chloride, thermoplastic elastomer, thermoplastic polyurethane, polyolefin, and silicone.

4. The peristaltic pumping segment of claim 1, wherein the check valve is configured to close after complete expansion of the pumping volume.

5. The peristaltic pumping segment of claim 1, wherein the check valve is configured to open after complete contraction of the pumping volume.

6. The peristaltic pumping segment of claim 1, wherein the check valve changes between an open configuration and a closed configuration in response to changing pressure differentials across the check valve.

7. The peristaltic pumping segment of claim 1, wherein the pumping segment is configured to operate with a peristaltic pump comprising a disabled upstream occluder.

* * * * *